United States Patent [19]

Pastor et al.

[11] Patent Number: 5,331,031
[45] Date of Patent: Jul. 19, 1994

[54] GAMMA CRYSTALLINE MODIFICATION OF 2,2',2''-NITRILO[TRIETHYL-TRIS(3,3',5,5'-TETRA-TERT-BUTYL-1,1'-BIPHENYL-2,2'-DIYL) PHOSPHITE]

[75] Inventors: Stephen D. Pastor, Danbury, Conn.; Sai P. Shum, Pleasantville, N.Y.; Paul A. Odorisio, Leonia, N.J.

[73] Assignee: Ciba-Geigy Corporation, Ardsley, N.Y.

[21] Appl. No.: 108,964

[22] Filed: Aug. 18, 1993

[51] Int. Cl.$^5$ .................... C07F 9/6574; C08K 5/52
[52] U.S. Cl. .................... 524/119; 558/78; 558/147
[58] Field of Search .................... 524/119; 558/78, 147

[56] References Cited

U.S. PATENT DOCUMENTS 4,318,845  3/1982  Spivack et al. .
4,374,219  2/1983  Spivack et al. .
4,683,326  7/1987  Orban et al. .

OTHER PUBLICATIONS

Pure & Applied Chemistry—vol. 45, pp. 11–30 Pergamon Press, 1976.

*Primary Examiner*—Veronica P. Hoke
*Attorney, Agent, or Firm*—Lurther A. R. Hall

[57] ABSTRACT

The gamma crystalline modification of 2,2',2''-nitrilo[triethyl-tris-(3,3',5,5'-tetra-tert-butyl-1,1'-biphenyl-2,2'-diyl)phosphite] is obtained by crystallizing or recrystallizing said compound from an alkanol of 4 to 8 carbon atoms.

The gamma crystalline form is an effective process stabilizer for polyolefins, particularly polypropylene.

6 Claims, No Drawings

GAMMA CRYSTALLINE MODIFICATION OF 2,2',2''-NITRILO[TRIETHYL-TRIS(3,3',5,5'-TETRA-TERT-BUTYL-1,1'-BIPHENYL-2,2'-DIYL) PHOSPHITE]

This invention pertains to a novel crystalline modification of 2,2',2''-nitrilo[triethyl-tris-(3,3',5,5'-tetra-tert-butyl-1,1'-biphenyl-2,2'-diyl) phosphite] and to processes for preparing said modification.

BACKGROUND OF THE INVENTION 2,2',2''-Nitrilo[triethyl-tris-(3,3',5,5'-tetra-tert-butyl-1,1'-biphenyl-2,2'-diyl) phosphite] is a compound having the formula I

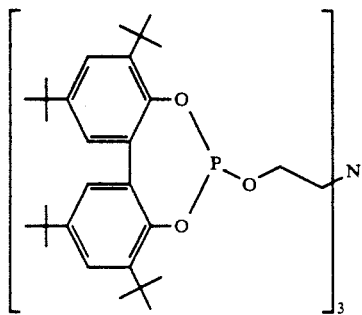

This compound of formula I is useful as a processing stabilizer for organic polymers as taught in U.S. Pat. Nos. 4,318,845 and 4,374,219. The compound of formula I is disclosed as being a white powder melting at 121°–134° C. As such, the powdery product has defects in terms of handling and apparent density, exhibiting poor flowability, meterability, storage stability, hydrolytic stability and compatibility in polymeric substrates and lubricating oils.

It has now been found that the compound of formula I can be obtained in a different crystalline modification as purified crystalline particles which exhibit acceptable properties in respect to handling, apparent density, flowability, meterability, storage stability, hydrolytic stability and compatibility in polymeric substrates and lubricating oils.

The new modification is characterized by a novel crystalline form, melting in the range of 178°–185° C. as given by the peak temperature of the endotherm recorded by differential scanning calorimetry (DSC); and by an X-ray diffraction pattern obtained using Cu-Kα which exhibits diffraction angles (2Θ) as seen below:

| Peak No. | Diffraction Angle |
| --- | --- |
| 1 | 5.4 |
| 2 | 6.3 |
| 3 | 8.8 |
| 4 | 9.9 |
| 5 | 10.3 |
| 6 | 10.8 |
| 7 | 11.7 |
| 8 | 13.8 |
| 9 | 14.8 |
| 10 | 15.5 |
| 11 | 16.1 |
| 12 | 17.0 |
| 13 | 17.7 |
| 14 | 18.4 |
| 15 | 20.2 |

The instant invention also relates to a process for the preparation of this novel gamma crystalline modification of the compound of formula I.

The instant invention also pertains to a composition stabilized against thermal, oxidative and actinic induced degradation which comprises
 (a) a polyolefin, and
 (b) an effective stabilizing mount (generally about 0.01 to about 5% by weight of the stabilized composition) of the gamma crystalline form of 2,2',2''-nitrilo[triethyl-tris-(3,3', 5,5'-tetra-tert-butyl-1,1'-biphenyl-2,2'-diyl) phosphite], characterized by melting in the range of 178°–185° C. and by an X-ray diffraction pattern obtained using a Cu-Kα which exhibits diffraction angles (2Θ) as seen below:

| Peak No. | Diffraction Angle |
| --- | --- |
| 1 | 5.4 |
| 2 | 6.3 |
| 3 | 8.8 |
| 4 | 9.9 |
| 5 | 10.3 |
| 6 | 10.8 |
| 7 | 11.7 |
| 8 | 13.8 |
| 9 | 14.8 |
| 10 | 15.5 |
| 11 | 16.1 |
| 12 | 17.0 |
| 13 | 17.7 |
| 14 | 18.4 |
| 15 | 20.2 |

Preferably, the polyolefin is polypropylene.

The process for the preparation of the gamma crystalline modification of the compound of formula I is crystallizing or recrystallizing the compound of formula I from an alkanol of 4 to 8 carbon atoms. Preferably the alkanol is an n-alkanol of 4 to 8 carbon atoms; most preferably 1-butanol or 1-octanol.

Some alkanols useful in the instant process are, for example, 1-butanol, sec-butyl alcohol, isobutyl alcohol, 1-pentanol, isoamyl alcohol, 1-hexanol, 2-ethyl-1-hexanol, 1-heptanol and 1-octanol.

Differential scanning calorimetry (DSC) measurements are obtained on a TA Instrument Inc., 910 differential scanning calorimeter, with a 100 mL/min nitrogen purge, aligned aluminum pan, temperature scan at 5° C./min to 230° C.

X-ray diffraction patterns are recorded on a Philips Norelco X-ray Diffractometer unit, using Cu-Kα radiation with a nickel filter. All samples have a uniform particle size of 40 to 75 microns. This is the same particle size distribution obtained with the prior an compound of Example 3.

EXAMPLE 1

The compound of formula I, 2,2',2''-nitrilo[triethyl-tris-(3,3', 5,5'-tetra-tert-butyl-1,1'-biphenyl-2,2'-diyl) phosphite], is prepared according to procedure of Example 4 of U.S. Pat. No. 4,318,845. A 10 g sample of the compound of formula (I) is recrystallized from 100 mL of 1-butanol to obtain 4.8 g of the novel crystal modification of the compound of formula (I) having a mp=182° C. (the melting point is determined by differential scanning calorimetry and the peak temperature in the endotherm is recorded as the melting point) and exhibiting an X-ray diffraction pattern obtained using Cu-Kα which exhibits diffraction angles (2Θ):

| Peak No. | Diffraction Angle | Relative Intensity (%) |
| --- | --- | --- |
| 1 | 5.4 | 100 |
| 2 | 6.3 | 38.0 |
| 3 | 8.8 | 19.0 |
| 4 | 9.9 | 43.7 |
| 5 | 10.3 | 39.4 |
| 6 | 10.8 | 74.6 |
| 7 | 11.7 | 9.2 |
| 8 | 13.8 | 27.5 |
| 9 | 14.8 | 17.6 |
| 10 | 15.5 | 39.4 |
| 11 | 16.1 | 33.1 |
| 12 | 17.0 | 47.9 |
| 13 | 17.7 | 50.0 |
| 14 | 18.4 | 34.7 |
| 15 | 20.2 | 33.8 |

Example 2

The compound of formula I is prepared according to the procedure of Example 4 of U.S. Pat. No. 4,318,845. A 5 g sample of the compound of formula I is recrystallized from 45 mL of 1-octanol to obtain 2.4 g of the novel crystal modification of the compound of formula (I) having a mp=178.6° C. (the melting point is determined by differential scanning calorimetry and the peak temperature in the endotherm is recorded as the melting point) and exhibiting an X-ray diffraction pattern obtained using Cu-Kα which exhibits diffraction angles (2Θ) (±0.2°) which are the same as that found for the gamma crystalline form prepared in Example 1.

Such data show that the gamma crystals prepared in Example 1 and Example 2 are essentially the same.

EXAMPLE 3

Comparative Example

A compound of formula I is prepared according to the procedure of Example 4 of U.S. Pat. No. 4,318,845. This compound exhibits an X-ray diffraction pattern obtain using Cu-Kα which exhibits diffraction angles (2Θ):

| Peak No. | Diffraction Angle | Relative Intensity (%) |
| --- | --- | --- |
| 1 | 5.0 | 100 |
| 2 | 5.7 | 47.2 |
| 3 | 7.0 | 8.0 |
| 4 | 7.9 | 30.4 |
| 5 | 8.8 | 40.0 |
| 6 | 10.6 | 57.6 |
| 7 | 11.5 | 21.6 |
| 8 | 13.5 | 22.4 |
| 9 | 14.3 | 21.6 |
| 10 | 15.6 | 37.6 |
| 11 | 16.1 | 44.0 |
| 12 | 16.5 | 65.6 |
| 13 | 16.9 | 43.2 |
| 14 | 17.3 | 74.4 |
| 15 | 18.3 | 48.8 |
| 16 | 18.6 | 21.6 |
| 17 | 19.5 | 23.2 |
| 18 | 20.3 | 16.8 |
| 19 | 20.8 | 20.0 |

A comparison of the X-ray diffraction patterns of the instant gamma modification as seen in Examples 1 and 2 with the X-ray diffraction pattern of the prior an compound of Example 4 of U.S. Pat. No. 4,318,845 clearly indicates that the two materials are not the same.

EXAMPLE 4

Process Stabilization of Propylene at 525° F. (274° C.)

When unstabilized polypropylene containing 0.075% by weight of calcium stearate is admixed with an effective amount of the gamma crystalline modification of the compound of formula I as prepared in Example 1 and then extruded from an extruder at 525° F. (274° C.), the melt flow rate (in grams/10 minutes) is determined by ASTM method D1238.

The instant gamma modification of the compound of formula I is particularly effective in stabilizing polypropylene against thermal and oxidative degradation as shown by a minimum change in the melt flow rate.

EXAMPLE 5

Hydrolytic Stability of Gamma Modification

To demonstrate the superior storage stability of the new gamma form, an accelerated test is performed on the instant compound of Example 2 and on the amorphous form of the compound of formula I prepared by heating the compound of Example 4 of U.S. Pat. No. 4,318,845 to 210° C. until a clear melt is obtained. The melt is cooled rapidly to ambient temperature to yield a glassy solid with a $T_g$(DSC) of 105°-110° C. which is amorphous.

The two test compounds are exposed to 80% humidity at 50° C. and the rate of hydrolysis is monitored by liquid chromatography. As a function of time, a greater mount of the gamma form is found remaining compared to the amorphous form after any given time of humidity exposure indicating that the gamma form would have superior storage stability compared to the amorphous fore of the compound of formula I.

What is claimed is:

1. A process for the preparation of the gamma crystalline form of the compound 2,2',2''-nitrilo[triethyl-tris-(3,3',5,5 '-tetra-tert-butyl-1,1'-biphenyl-2,2'-diyl) phosphite]characterized by melting in the range of 178°-185° C. and by an X-ray diffraction pattern obtained using Cu-Kα which exhibits diffraction angles (2Θ):

| Peak No. | Diffraction Angle |
| --- | --- |
| 1 | 5.4 |
| 2 | 6.3 |
| 3 | 8.8 |
| 4 | 9.9 |
| 5 | 10.3 |
| 6 | 10.8 |
| 7 | 11.7 |
| 8 | 13.8 |
| 9 | 14.8 |
| 10 | 15.5 |
| 11 | 16.1 |
| 12 | 17.0 |
| 13 | 17.7 |
| 14 | 18.4 |
| 15 | 20.2 | which comprises, crystallizing or recrystallizing said compound from an alkanol of 4 to 8 carbon atoms.

2. A process according to claim 1 wherein the alkanol is an n-alkanol.

3. A process according to claim 2 wherein the n-alkanol is 1-butanol or 1-octanol.

4. The gamma crystalline form of 2,2',2''-nitrilo[-triethyl-tris-(3,3',5,5'-tetra-tert-butyl-1,1'-biphenyl-2,2'-diyl) phosphite], characterized by melting in the range of 178°–185° C. and by an X-ray diffraction pattern obtained using Cu-Kα which exhibits diffraction angles (2Θ):

| Peak No. | Diffraction Angle |
|---|---|
| 1 | 5.4 |
| 2 | 6.3 |
| 3 | 8.8 |
| 4 | 9.9 |
| 5 | 10.3 |
| 6 | 10.8 |
| 7 | 11.7 |
| 8 | 13.8 |
| 9 | 14.8 |
| 10 | 15.5 |
| 11 | 16.1 |
| 12 | 17.0 |
| 13 | 17.7 |
| 14 | 18.4 |
| 15 | 20.2 |

5. A composition stabilized against thermal, oxidative and actinic induced degradation which comprises
   (a) a polyolefin, and
   (b) an effective stabilizing mount of the gamma crystalline form of 2,2',2''-nitrilo-[triethyl-tris-(3,3',5,5'-tetra-tert-butyl-1,1'-biphenyl-2,2'-diyl) phosphite], characterized by melting in the range of 178°–185° C. and by an X-ray diffraction pattern obtained using Cu-Kα which exhibits diffraction angles (2Θ):

| Peak No. | Diffraction Angle |
|---|---|
| 1 | 5.4 |
| 2 | 6.3 |
| 3 | 8.8 |
| 4 | 9.9 |
| 5 | 10.3 |
| 6 | 10.8 |
| 7 | 11.7 |
| 8 | 13.8 |
| 9 | 14.8 |
| 10 | 15.5 |
| 11 | 16.1 |
| 12 | 17.0 |
| 13 | 17.7 |
| 14 | 18.4 |
| 15 | 20.2 |

6. A composition according to claim 5 wherein the polyolefin is polypropylene.

* * * * *